United States Patent [19]

Baxter et al.

[11] Patent Number: 5,763,459

[45] Date of Patent: Jun. 9, 1998

[54] MEDICAMENTS FOR THE TREATMENT OF ANXIETY

[75] Inventors: Gordon Smith Baxter, Cole Green, Great Britain; Guy Anthony Kennett, Epping, England

[73] Assignee: SmithKline Beecham p.l.c., Brentford, England

[21] Appl. No.: 341,577

[22] PCT Filed: May 18, 1993

[86] PCT No.: PCT/GB93/01013

§ 371 Date: Feb. 28, 1995

§ 102(e) Date: Feb. 28, 1995

[87] PCT Pub. No.: WO93/24117

PCT Pub. Date: Dec. 9, 1993

[30] Foreign Application Priority Data

| May 23, 1992 | [GB] | United Kingdom | 9211082 |
| Jul. 7, 1992 | [GB] | United Kingdom | 9214399 |
| Sep. 12, 1992 | [GB] | United Kingdom | 9219356 |
| Dec. 29, 1992 | [GB] | United Kingdom | 9227045 |

[51] Int. Cl.⁶ ............. A61K 31/445; A61K 31/415; A61K 31/24

[52] U.S. Cl. ............. 514/323; 514/331; 514/393; 514/535

[58] Field of Search ............. 514/304, 323, 514/331, 393, 535

[56] References Cited

FOREIGN PATENT DOCUMENTS

| 0 076 530 | 4/1983 | European Pat. Off. . |
| 0 229 444 | 7/1987 | European Pat. Off. . |
| 0 278 173 | 8/1988 | European Pat. Off. . |
| 0 309 423 | 3/1989 | European Pat. Off. . |
| 0 501 322 A1 | 9/1992 | European Pat. Off. . |
| 0 505 322 A1 | 9/1992 | European Pat. Off. . |
| 2 674 853 | 10/1992 | France . |
| WO 93/05040 | 3/1983 | WIPO . |
| WO 90/12569 | 11/1990 | WIPO . |
| WO 93/02677 | 2/1993 | WIPO . |
| WO 93/03725 | 3/1993 | WIPO . |
| WO 93/05038 | 3/1993 | WIPO . |
| WO 93/08187 | 4/1993 | WIPO . |
| WO 93/14745 | 8/1993 | WIPO . |
| WO 93/16072 | 8/1993 | WIPO . |

*Primary Examiner*—William R.A. Jarvis
*Attorney, Agent, or Firm*—Soma G. Simon; Charles M. Kinzig; Edward T. Lentz

[57] ABSTRACT

A method for the treatment of anxiety in mammals comprises administering an effective amount of a 5-HT$_4$ receptor antagonist.

5 Claims, No Drawings

MEDICAMENTS FOR THE TREATMENT OF ANXIETY

This application is a 371 of PCT/GB93/01013, filed 05/18/93.

This invention relates to a method of treatment of anxiety in mammals, including humans.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT4 receptor.

EP-A-501322 (Glaxo Group Limited), WO 93/02677, WO 93/03725, WO 93/05038, WO 93/05040 and PCT/GB93/00506 (SmithKline Beecham plc) describe compounds having 5-HT$_4$ receptor antagonist activity.

For instance, WO 93/02677 describes compounds of formula (I), or a pharmaceutically acceptable salt thereof

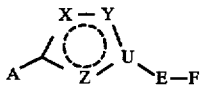
(I)

wherein the dotted circle represents one or two double bonds in any position in the 5-membered ring; X, Y and Z independently represent oxygen, sulphur, nitrogen or carbon, provided that at least one of X, Y and Z represents oxygen, sulphur or nitrogen; U represents nitrogen or carbon;

A represents a group of formula (II):

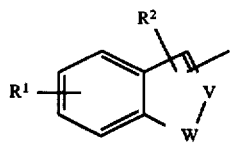
(II)

in which:

R$^1$ represents hydrogen, hydroxy, C$_{1-6}$ alkyl, C$_{2-6}$ alkenyl, C$_{2-6}$ alkynyl, (C$_{1-6}$ alk alkoxy, hydroxy (C$_{1-6}$) alkyl, halogen, amino, cyano, —CONR$^6$R$^7$ or —SO$_2$NR$^6$R$^7$, in which R$^6$ and R$^7$ independently represents hydrogen, C$_{1-6}$ alkyl, C$_{2-6}$ alkenyl or C$_{2-6}$ alkynyl;

R$^2$ represents hydrogen, halogen, C$_{1-6}$ alkyl, C$_{1-6}$ alkoxy or C$_{1-6}$ alkylcarbonyl;

V represents nitrogen,

—CH or —C— and

W represents oxygen, sulphur or

—NR$^8$ in which

R$^8$ represents hydrogen, C$_{1-6}$ alkyl, C$_{2-6}$ alkenyl or C$_{2-6}$ alkynyl;

E represents a straight or branched alkylene or alkenylene chain containing from 1 to 5 carbon atoms and optionally containing an —O—, —S—, —NH— or —Nalkyl— linkage; and F represents:

a) a non-aromatic azacyclic ring system or a non-aromatic azabicyclic ring system having carbon bridgehead(s); or b) a group of formula —NR$^a$R$^b$ wherein one of R$^a$ and R$^b$ is hydrogen or C$_{1-6}$ alkyl and the other is hydrogen, C$_{1-10}$ alkyl, C$_{2-6}$ alkenyl, C$_{2-6}$ alkynyl or aryl(C$_{1-6}$)alkyl.

WO 93/05040 describes compounds of formula (III), or a pharmaceutically acceptable salt thereof

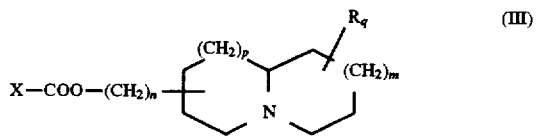
(III)

wherein

X is of sub-formula (a) or (b):

(a)

(b)

wherein

L is N or CR$_c$ wherein R$_c$ is hydrogen, C$_{1-6}$ alkoxy, halo, C$_{1-6}$ alkyl or cyano;

Q is NR$_1$, CH$_2$, O or S;

R$_a$ is hydrogen, halo, C$_{1-6}$ alkyl, amino, nitro or C$_{1-6}$ alkoxy;

R$_b$ is hydrogen, halo, C$_{1-6}$ alkyl or C$_{1-6}$ alkoxy;

R$_1$ is hydrogen, C$_{1-10}$ alkyl, C$_{2-6}$ alkenyl, aralkyl, C$_{2-6}$ alkanoyl, or C$_{2-6}$ alkanoyl C$_{1-3}$ alkyl;

R$_2$ is C$_{1-6}$ alkoxy; and

R$_3$ is hydrogen, chloro or fluoro;

R$_4$ is hydrogen, C$_{1-6}$ alkyl, amino optionally substituted by a C$_{1-6}$ alkyl group, halo, hydroxy or C$_{1-6}$ alkoxy; R$_5$ is hydrogen, halo, C$_{1-6}$ alkyl, C$_{1-6}$ alkoxy, nitro, amino or C$_{1-6}$ alkylthio; R$_6$ is hydrogen, halo, C$_{1-6}$ alkyl, C$_{1-6}$ alkoxy or amino;

n is 0, 1, 2, 3 or 4;

p and m are independently 0, 1 or 2; and

R$_q$ is hydrogen or C$_{1-6}$ alkyl.

WO 93/03725 describes compounds of formula (IV) or a pharmaceutically acceptable salt thereof;

X—CO—Y—Z (IV)    (IV)

wherein

X is a group of formula (a), (b) or (c):

(a)

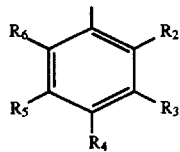
(b)

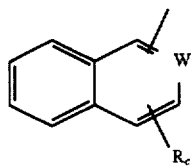
(c)

wherein

L is N or $CR_S$ wherein $R_S$ is hydrogen, $C_{1-6}$ alkoxy, halogen, $C_{1-4}$ alkyl or cyano;

Q is $NR_1$, $CH_2$, O or S;

W is CH or N;

$R_a$ is hydrogen, halo, $C_{1-6}$ alkyl, amino, nitro or $C_{1-6}$ alkoxy;

$R_b$ is hydrogen, halo, $C_{1-6}$ alkyl or $C_{1-6}$ alkoxy;

$R_1$ is hydrogen, $C_{1-10}$ alkyl, $C_{2-6}$ alkenyl, aralkyl, $C_{2-6}$ alkanoyl or $C_{2-6}$ alkanoyl $C_{1-3}$ alkyl;

$R_2$ is $C_{1-6}$ alkoxy; and $R_3$ is hydrogen, chloro or fluoro;

$R_4$ is hydrogen, $C_{1-6}$ alkyl, amino optionally substituted by a $C_{1-6}$ alkyl group, halo, hydroxy or $C_{1-6}$ alkoxy;

$R_5$ is hydrogen, halo, $C_{1-6}$ alkyl, $C_{1-6}$ alkoxy, nitro, amino or $C_{1-6}$ alkylthio; and $R_6$ is hydrogen, halo, $C_{1-6}$ alkyl, $C_{1-6}$ alkoxy or amino;

$R_c$ is hydrogen, $C_{1-6}$ alkoxy, halo or $C_{1-6}$ alkyl;

Y is O or NH;

Z is of sub-formula (d) or (e):

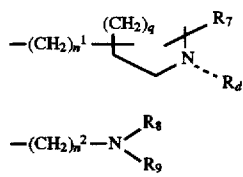

wherein $n^1$ is 0, 1, 2, 3 or 4; $n^2$ is 2, 3, 4 or 5;

q is 0, 1, 2, or 3;

$R_d$ is hydrogen, $C_{1-12}$ alkyl or aralkyl;

$R_7$ and $R_8$ are hydrogen or $C_{1-6}$ alkyl; and $R_9$ is hydrogen or $C_{1-10}$ alkyl;

WO 93/05038 describes compounds of formula (V) and pharmaceutically acceptable salts thereof:

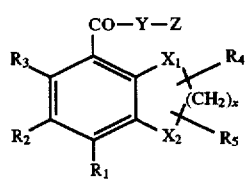

in which $X_1$—$(CH_2)_x$—$X_2$ forms a 5–7 membered ring wherein:

$X_1$ is O or or S;

$X_2$ is O, S, NR or NRCO wherein R is hydrogen or $C_{1-6}$ alkyl;

x is 1, 2 or 3;

$R_1$ is hydrogen, amino, halo, $C_{1-6}$ alkyl, hydroxy or $C_{1-6}$ alkoxy;

$R_2$ is hydrogen, halo, $C_{1-6}$ alkyl, $C_{1-6}$ alkoxy, nitro, amino or $C_{1-6}$ alkylthio;

$R_3$ is hydrogen, halo, $C_{1-6}$ alkyl, $C_{1-6}$ alkoxy or amino;

$R_4$ and $R_5$ are independently hydrogen or $C_{1-6}$ alkyl;

Y is O or NH;

Z is of sub-formula (a), (b) or (c):

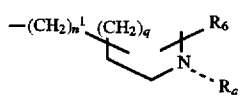
(a)

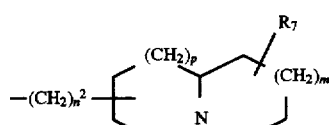
(b)

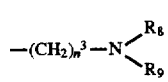
(c)

wherein

—$(CH_2)_n^1$ is attached at carbon or nitrogen and $n^1$ is 1, 2, 3 or 4; $n^2$ is 1 or 2; $n^3$ is 2, 3, 4 or 5;

q is 0, 1, 2 or 3; p is 0, 1 or 2; m is 0, 1 or 2;

$R_a$ is hydrogen or a lipophilic group, such as $C_{1-12}$ alkyl or aralkyl;

$R_6$, $R_7$ and $R_8$ are independently hydrogen or $C_{1-6}$ alkyl; and $R_9$ is hydrogen or $C_{1-10}$ alkyl;

or a compound of formula (V) wherein the CO—Y linkage is replaced by a heterocyclic bioisostere.

PCT/GB93/00506 describes compound of formula (VI), or a pharmaceutically acceptable salt thereof

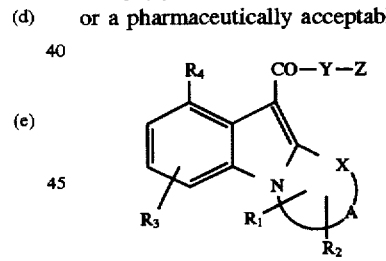
(VI)

wherein

X is O, S, SO, $SO_2$, $CH_2$, CH or NR wherein R is hydrogen or $C_{1-6}$ alkyl;

A is a saturated or unsaturated polymethylene chain of 2–4 carbon atoms;

$R_1$ and $R_2$ are hydrogen or $C_{1-6}$ alkyl;

$R_3$ is hydrogen, halo, $C_{1-6}$ alkyl, amino, nitro or $C_{1-6}$ alkoxy;

$R_4$ is hydrogen, halo, $C_{1-6}$ alkyl or $C_{1-6}$ alkoxy;

Y is O or NH;

Z is of sub-formula (a), (b) or (c):

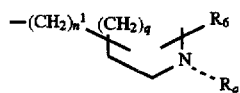
(a)

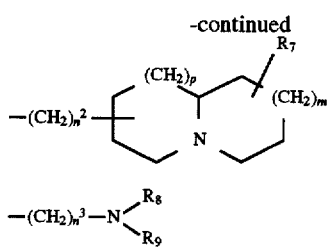

wherein $n^1$ is 1, 2, 3 or 4; $n^2$ is 0, 1, 2, 3 or 4; $n^3$ is 2, 3, 4 or 5; q is 0, 1, 2 or 3; p is 0, 1 or 2; m is 0, 1 or 2;

$R_5$ is hydrogen, $C_{1-12}$ alkyl, aralkyl or $R_5$ is $(CH_2)_z$—$R_{10}$ wherein $R_{10}$ is selected from cyano, hydroxyl, $C_{1-6}$ alkoxy, phenoxy, $C(O)C_{1-6}$ alkyl, $COC_6H_5$, —$CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; and $R_6$, $R_7$ and R8 are independently hydrogen or $C_{1-6}$ alkyl; and $R_9$ is hydrogen or $C_{1-10}$ alkyl;

or a compound of formula (VI) wherein the CO—Y linkage is replaced by a heterocyclic bioisostere.

Some 5-HT$_3$ receptor antagonists have been disclosed as of potential use in the treatment of anxiety (see GB 2153821A, EP-A-229444 (Glaxo Group Ltd.) and EP-A-201165 (Beecham Group p.l.c)).

We have now discovered that a compound which acts as an antagonist at 5-HT$_4$ receptors is of potential use in the treatment of anxiety, such as general anxiety disorder (GAD), mixed anxiety/depression or panic disorder.

The conditions under which anxiolysis is observed for this compound in the elevated X-maze differs from those required for the observation of the anxiolytic effects of 5-HT$_3$ receptor antagonists. Furthermore the site of action of 5-HT$_3$ receptor antagonists is thought to be the amygdala (Higgins et al 1991, Pschopharmacology, 104, 545–551), while 5-HT$_4$ receptor mediated anxiolysis is likely to be effected via the hippocampus (Dumuis et al 1988, Mol Pharmacol., 34, 880–887).

The invention therefore provides a method for the treatment and/or prophylaxis of anxiety in mammals, including humans, which method comprises administering to the mammal in need of such treatment and/or prophylaxis, an effective and/or prophylactic amount of a 5-HT$_4$ receptor antagonist.

5-HT$_4$ receptor antagonists may be identified according to standard methods, such as that described hereinafter, and the methods described in Naunyn-Schmiedeberg's Arch Pharmacol. 342, 619–622 and 343, 439–446, and J. Pharamcol. Exp. Ther. (1990) 252, 1378–1386.

Examples of 5-HT$_4$ receptor antagonists include R 50 595 (Janssen), which is described in FR76530 and Eur. J. Pharmacol., 181 119–125 (1990), SDZ 205–557 (2-diethylaminoethyl-(2-methoxy-4-amino5-chloro) benzoate), which is described by K. H. Buchheit and R. Gamse in Naunyn-Schmiedeberg's Arch. Pharmacol., 343 (Suppl.), R101 (1991) and 345, 387–393 (1992), DAU 6215 endo-2,3-dihydro-N-(8-methyl-8-azabicyclo[3.2.1]oct-3-yl) -2-oxo-1H-benzimidazole-1-carboxamide; Br. J. Pharmacol. (1991), 104, Proc. Supp. 47 P, DAU 6285 (2,3-dihydro-6-methoxy-2-oxo-1H-benzimidazole-1-carboxylic acid endo-8-methyl-8-azabicyclo[3.2.1oct-3-yl ester; Naunyn-Schmiedeberg's Arch. Pharmacol, 345; 264–269 (1992), RS 23597–190 (1-[3-[[(4-amino-5-chloro-2-methoxy)benzoyl] oxy]propyl]piperidinium; (Syntex-British Pharmacology Society Meeting, September 1992), SC 53606 1-[3-[[4-amino-5-chloro-2-methoxy)benzoyl]oxy]propyl] piperidinium (RS2359190); (1-S,8-S)-N-[hexahydro-1H-pyrrolizin-1-yl)methyl]6-chloroimidazo[1,2-a]pyridine-8-carboxamid (Searle-2nd International Symposium on Serotonin, Houston, USA,—September 1992) and GR113808 (1-methyl-1H-indole-3-carboxylic acid[1-[2-[methylsulfonyl)amino]ethyl]-4-piperidinyl]methyl ester; (Glaxo—EP-A-501322).

ICS 205-930 (tropisetron), which is described in GB 2125398A (Sandoz Limited) is also a 5-HT$_4$ receptor antagonist, but is far more potent as a 5-HT$_3$ receptor antagonist.

In a preferred aspect, the 5-HT$_4$ receptor antagonist is a more potent antagonist at 5-HT$_4$ receptors than at 5-HT$_3$ receptors.

Preferably, the 5-HT$_4$ receptor antagonist is in substantially pure pharmaceutically acceptable form.

The administration of the 5-HT$_4$ receptor antagonist may be by way of oral, sublingual, transdermal or parenteral administration.

An amount effective to treat the disorder hereinbefore described depends on the usual factors such as the nature and severity of the disorder being treated and the weight of the mammal. However, a unit dose will normally contain 0.1 to 50 mg for example 0.5 to 10 mg, of the 5-HT$_4$ receptor antagonist, such as a compound of formula (I) or a pharmaceutically acceptable salt thereof. Unit doses will normally be administered once or more than once a day, for example 2, 3, or 4 times a day, more usually 1 to 3 times a day, such that the total daily dose is normally in the range, for a 70 kg adult of 0.1 to 50 mg, for example 0.1 to 5 mg, that is in the range of approximately 0.001 to 1 mg/kg/day, more usually 0.005 to 0.2 mg/kg/day.

For oral or parenteral administration, it is greatly preferred that the 5-HT$_4$ receptor antagonist is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the 5-HT$_4$ receptor antagonist and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the treatment concerned.

The present invention also provides the use of a 5-HT$_4$ receptor antagonist in the manufacture of a medicament for use in the treatment and/or prophylaxis of anxiety. Such treatment and/or prophylaxis may be carried out as hereinbefore described.

The present invention further provides a pharmaceutical composition for use in the treatment and/or prophylaxis of anxiety which comprises a 5-HT$_4$ receptor antagonist, and a pharmaceutically acceptable carrier. Such compositions may be prepared in the manner as hereinbefore described.

5-HT$_5$ receptor antagonist activity

Male guinea-pigs, weighing 250–400 g were used. Longitudinal muscle-myenteric plexus preparations, approximately 3cm long, were obtained from the distal colon region. These were suspended under a 0.5 g load in isolated tissue baths containing Krebs solution bubbled with 5% $CO_2$ in $O_2$ and maintained at 37° C. In all experiments, the Krebs solution also contained methiothepin $10^{-7}$M, methysergide $2\times10^{-7}$M and granisetron $10^{-6}$M.

After construction of a simple concentration-response curve with 5-HT, using 30 s contact times and a 15 min dosing cycle, a concentration of 5-HT is selected so as to obtain a contraction of the muscle approximately 40–70% maximum (10–9M approx). The tissue is then alternately dosed every 15min with this concentration of 5-HT and then with an approximately equi-effective concentration of the nicotine receptor stimulant (dimethylphenyl piperazinium) DMPP. After obtaining consistent responses to both 5-HT and DMPP, increasing concentrations of a putative 5-HT$_4$ receptor antagonist are then added to the bathing solution. The effects of this compound are then determined as a percentage reduction of the contractions evoked by 5-HT or by DMPP. From this data, IC$_{50}$ values are determined, being defined as the concentration of antagonist which reduced the contraction by 50%. A compound which reduced the response to 5-HT but not to DMPP is believed to act as a 5-HT$_4$ receptor antagonist.

In Vivo Testing

Social Interation

Rats (male, Sprague Dawleys, Charles River, 250–300 g) are housed in groups of eight in a holding room for 5 days. They are then housed singly in a room adjacent to the experimental room for 4 days prior to the experimental day. On the experimental day rats are administered vehicle, test compound or a benzodiazepine anxiolytic, chlordiazepoxide, S.C. in pairs (n=8–16), at 15 minute intervals beginning at 10.00 am. 30 mins. later they are placed with a weight matched pair-mate (encountered for the first time) in the social interaction box in a separate room. The box is made of white perspex 54 cm$\times$37 cm$\times$26 cm with a transparent perspex front side and no lid. The floor is divided up into 24 squares and the box is brightly lit (115 lux). Active social interactive behaviours (grooming, sniffing, climbing over or under, following, biting, mounting and boxing) are scored blind for 15 min. by remote vido monitoring to give total interaction scores. The number of squares crossed by each rat is also scored and summed. After the end of each text the box is carefully wiped.

X-Maze

The X-maze is raised 50 cm above the floor and consists of two enclosed arms 45 cm (long)$\times$10 cm (wide) and 10 cm (high) and two open arms 45$\times$10$\times$1 cm, arranged such that the two arms of each type are opposite each other. Both arm types are marked into two equal sections. Rats are placed onto the centre of the X-maze and observed for a period of five min. during which time the following parameters are recorded: 1). The number of entries on to, and the time spent on, (a) open arms (b) closed arms, (c) end of open arms and (d) end of closed arms. 2) the number of sections crossed. The fear drive evoked in the open arms exceeds that in the closed arms and rats typically show a clear preference for the enclosed arms. Anxiolytic drugs increase the number of entries made onto, and the time spent on, the outer half of the open arms, and also the percentage of entries made onto, and the time spent on, the whole of the open arms. These four measures of anxiety, and also the total number of sections traversed, are calculated for each animal.

We claim:

1. A method for the treatment and/or prophylaxis of anxiety in a mammal in need thereof which method comprises administering to said mammal an effective or prophylactic amount of a 5-HT$_4$ receptor antagonist.

2. A method according to claim 1 wherein the 5-HT$_4$ receptor antagonist is more potent at 5-HT$_4$ receptors than at 5-HT$_3$ receptors.

3. A method according to claim 2 wherein the anxiety is general anxiety disorder (GAD) or mixed anxiety/depression.

4. A method according to claim 1, wherein the anxiety is panic disorder.

5. A method according to claim 1 wherein the 5-HT$_4$ receptor antagonist is:

2-diethylaminoethyl-(2-methoxy-4-amino-5-chloro) benzoate (SDZ205-557);

1-[3-[[(4-amino-5-chloro-2-methoxy)benzoyl]oxy] propyl]piperidinium (RS 23597-190); (1-S, 8-S)-N-[hexahydro-1H-pyrrolizin-1-yl)methyl]6-chloroimidazo[1,2-a]pyridine-8- carboxamide hydrochloride (SC 53606); or 1-methyl-1H-indole-3-carboxylic acid [1-[2-[methylsulfonyl)amino]ethyl]-4-piperidinyl]methyl ester (GR 108359), ester (GR 108359).

* * * * *